United States Patent
Ohki et al.

(10) Patent No.: US 9,597,033 B2
(45) Date of Patent: Mar. 21, 2017

(54) BIOLOGICAL-INFORMATION OBTAINING APPARATUS AND METHOD THEREOF

(75) Inventors: Mitsuharu Ohki, Tokyo (JP);
Tomonori Masuno, Tokyo (JP)

(73) Assignee: Sony Corporation, Tokyo (JP)

( * ) Notice: Subject to any disclaimer, the term of this patent is extended or adjusted under 35 U.S.C. 154(b) by 2792 days.

(21) Appl. No.: 12/110,537

(22) Filed: Apr. 28, 2008

(65) Prior Publication Data

US 2008/0306366 A1 Dec. 11, 2008

(30) Foreign Application Priority Data

Jun. 6, 2007 (JP) ................................. 2007-149857

(51) Int. Cl.
| | |
|---|---|
| A61B 5/00 | (2006.01) |
| A61B 5/1455 | (2006.01) |
| G06F 21/32 | (2013.01) |
| G06T 7/00 | (2006.01) |

(52) U.S. Cl.
CPC ........ *A61B 5/6826* (2013.01); *A61B 5/14551* (2013.01); *A61B 5/6838* (2013.01);
(Continued)

(58) Field of Classification Search
CPC . A61B 5/14551; A61B 5/0059; A61B 5/0062; A61B 5/0064; A61B 5/0075;
(Continued)

(56) References Cited

U.S. PATENT DOCUMENTS

| | | | |
|---|---|---|---|
| 4,832,484 A | 5/1989 | Aoyagi et al. | |
| 4,883,353 A | * 11/1989 | Hausman ........... | A61B 5/02433 128/205.12 |

(Continued)

FOREIGN PATENT DOCUMENTS

| | | |
|---|---|---|
| JP | 63-111837 | 5/1988 |
| JP | 6-98881 | 4/1994 |

(Continued)

OTHER PUBLICATIONS

Office Action issued Dec. 6, 2011 in Japan Application No. 2007-149857.
(Continued)

*Primary Examiner* — Adam J Eiseman
(74) *Attorney, Agent, or Firm* — Oblon, McClelland, Maier & Neustadt, L.L.P.

(57) ABSTRACT

A biological-information obtaining apparatus includes a light-emitting unit configured to emit light, an image-capturing unit configured to capture images, in time sequence, obtained by irradiating a living body with the light emitted and by causing the light to be transmitted through or reflected by the living body, the image-capturing unit being sensitive to at least two color components, an extreme generation unit configure to generate, for each of the captured images in the time sequence, a maximum value and a minimum value of each of the color components in a certain area of the captured image, and an oxygen-saturation calculation unit configured to calculate oxygen saturation on the basis of the maximum value and the minimum value of each of the color components in the certain area of the captured image.

9 Claims, 4 Drawing Sheets

(52) U.S. Cl.
CPC ............ *G06F 21/32* (2013.01); *G06T 7/0012* (2013.01); *G06T 2207/10016* (2013.01); *G06T 2207/10024* (2013.01); *G06T 2207/30101* (2013.01)

(58) Field of Classification Search
CPC ... A61B 5/0077; A61B 5/0261; A61B 5/1455; A61B 5/14552; G06T 2207/30004; G06T 2207/30088; G06T 2207/30076; G06T 7/0012; G06T 7/0014; G06T 7/0016
USPC ......... 600/322–328, 330–334, 336, 339–341
See application file for complete search history.

(56) References Cited

U.S. PATENT DOCUMENTS

| | | | |
|---|---|---|---|
| 5,408,998 A | * | 4/1995 | Mersch .................... 600/334 |
| 5,512,940 A | * | 4/1996 | Takasugi et al. ............. 348/71 |
| 2005/0001589 A1 | | 1/2005 | Edington et al. |
| 2005/0001629 A1 | | 1/2005 | Chen |
| 2009/0299154 A1 | * | 12/2009 | Segman .................... 600/301 |

FOREIGN PATENT DOCUMENTS

| | | |
|---|---|---|
| JP | 9-297166 | 11/1997 |
| JP | 2001-33381 | 2/2001 |
| JP | 2004-147408 | 5/2004 |
| WO | WO 2006100685 A2 * | 9/2006 |

OTHER PUBLICATIONS

U.S. Appl. No. 12/110,537, filed Apr. 28, 2008, Ohki, et al.
U.S. Appl. No. 12/131,640, filed Jun. 2, 2008, Ohki, et al.
Battery pack security and authentication IC for portable applications (bq SECURE™), Texas Instruments, XP-002498921, SLUS641A, Jan. 2005, 16 pages.

* cited by examiner

BIOLOGICAL-INFORMATION OBTAINING APPARATUS AND METHOD THEREOF

CROSS REFERENCES TO RELATED APPLICATIONS

The present invention contains subject matter related to Japanese Patent Application JP 2007-149857 filed in the Japanese Patent Office on Jun. 6, 2007, the entire contents of which are incorporated herein by reference.

BACKGROUND OF THE INVENTION

1. Field of the Invention

The present invention relates to a biological-information obtaining apparatus, particularly to a biological-information obtaining apparatus capable of obtaining information on oxygen saturation and a processing method thereof.

2. Description of the Related Art

The oxygen saturation represents the proportion of hemoglobin (Hb) that is oxyhemoglobin of blood. The hemoglobin of blood transports oxygen. The oxygen saturation is used as an index regarding a health condition of a living body, especially regarding a respiratory condition of the living body. As a medical device for determining oxygen saturation, for example, a pulse oximeter is known. A pulse oximeter is a device that noninvasively determines the oxyhemoglobin content of blood on the basis of the absorbance in a case in which a surface of a living body (for example, a finger tip) is irradiated with light of a certain wavelength and light of another wavelength.

For example, a pulse oximeter is known that obtains data on the absorbance of red light (a wavelength of 660 nm) and data on the absorbance of infrared light (a wavelength of 940 nm) by switching between light emission from a light-emitting diode that emits the red light and light emission from a diode that emits the infrared light, and calculates the oxygen saturation (see Japanese Unexamined Patent Application Publication No. 6-98881, FIG. 1).

SUMMARY OF THE INVENTION

In the above-described example of the related art, the oxygen saturation is noninvasively determined by obtaining data on the absorbance of the light with which the living body has been irradiated. However, in the above-described example of the related art, it is assumed that light sources of two different wavelengths are used. Therefore, a light-emitting driving device that causes the light sources to alternately emit light is necessary.

It is desirable to be able to calculate the oxygen saturation on the basis of one light source.

According to an embodiment of the present invention, there is provided a biological-information obtaining apparatus including light-emitting means for emitting light, image-capturing means for capturing images, in time sequence, obtained by irradiating a living body with the light emitted and by causing the light to be transmitted through or reflected by the living body, the image-capturing means being sensitive to at least two color components, extreme generation means for generating a maximum value and a minimum value, in time sequence of each of the color components for certain regions of the captured images, and oxygen-saturation calculation means for calculating oxygen saturation on the basis of the maximum value and the minimum value of each of the color components. This allows, for each of the at least two color components, generation of extremes and calculation of oxygen saturation on the basis of the extremes.

The light-emitting means may emit white light. The color components may include red and blue. According to an embodiment of the present invention, an example in which the combination of the red and blue components is used will be described; however, different colors may be used.

The extreme generation means may generate, for each of the color components, the maximum value and the minimum value in the time sequence from averages of the color component for the entirety of the captured images, or from averages of the color component for central regions of the captured images. If an image of a finger does not appear in peripheral areas of the captured images, the latter case may effectively be able to generate the maximum value and the minimum value.

According to another embodiment of the present invention, there is provided a biological-information obtaining apparatus including light-emitting means for emitting white light, image-capturing means for capturing images, in time sequence, obtained by irradiating a living body with the light emitted and by causing the light to be transmitted through or reflected by the living body, the image-capturing means being sensitive to at least red and blue color components, extreme generation means for generating a maximum value and a minimum value, in time sequence, of each of the color components for certain regions of the captured images, and oxygen-saturation calculation means for calculating, on the basis of the maximum value and the minimum value of each of the color components, oxygen saturation by solving an equation of $\{(Rc-Bc)-(Re-Be)\}/\{Bc-Be\}=[(Re-Be)\times\{S\times Eo(\lambda 1)+(1-S)\times Er(\lambda 1)\}]/[Be\times\{S\times Eo(\lambda 2)+(1-S)\times Er(\lambda 2)\}]$, where Rc represents the maximum value of the red component, Bc represents the maximum value of the blue component, Re represents the minimum value of the red component, Be represents the minimum value of the blue component, S represents oxygen saturation, $Eo(\lambda)$ represents a known absorbance coefficient of oxyhemoglobin at a wavelength $\lambda$, $Er(\lambda)$ represents a known absorbance coefficient of deoxyhemoglobin at a wavelength $\lambda$, and $\lambda 1$ and $\lambda 2$ represent specific values of wavelength $\lambda$. This allows, for each of the red and blue components, generation of the extremes and calculation of the oxygen saturation on the basis of the extremes.

According to another embodiment of the present invention, there is provided a method of obtaining biological information, the method being performed by a biological-information obtaining apparatus including light-emitting means for emitting white light, and image-capturing means for capturing images, in time sequence, obtained by irradiating a living body with the light emitted and by causing the light to be transmitted through or reflected by the living body, the image-capturing means being sensitive to at least red and blue color components. The method includes the steps of generating a maximum value and a minimum value, in time sequence, of each of the color components for certain regions of the captured images, and calculating oxygen saturation by solving the above-described equation. This allows, for each of the red and blue components, generation of the extremes and calculation of the oxygen saturation on the basis of the extremes.

According to the embodiments of the present invention, the oxygen saturation may be calculated on the basis of one light source.

DESCRIPTION OF THE PREFERRED EMBODIMENTS

Embodiments of the present invention will be described in detail with reference to the attached drawings.

Figure 1:
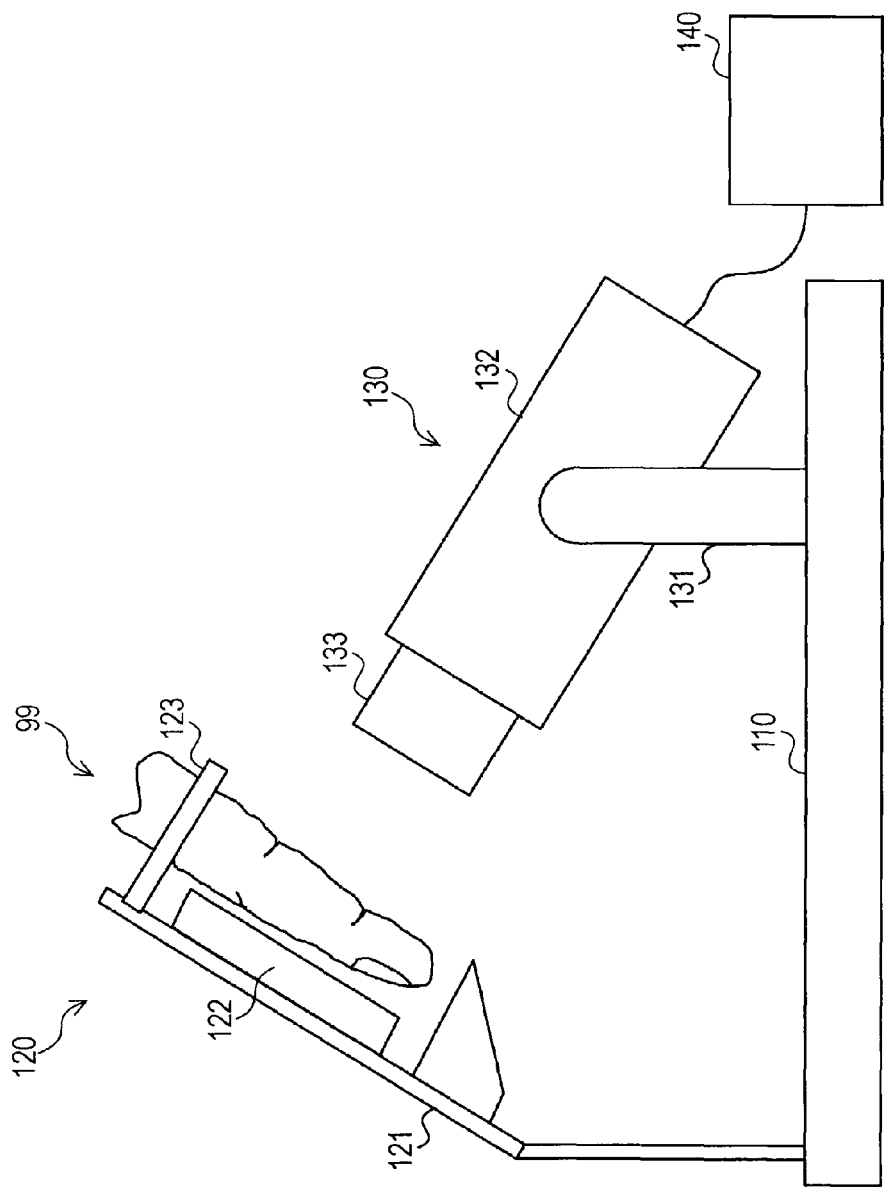
FIG. 1 is a diagram showing an exemplary side view of a biological-information obtaining apparatus according to an embodiment of the present invention.

FIG. 1 is a diagram showing an exemplary side view of a biological-information obtaining apparatus according to an embodiment of the present invention. In this biological-information obtaining apparatus, an irradiation unit 120 and an image-capturing unit 130 are provided on a base 110.

The irradiation unit 120 includes a support portion 121, a light-emitting portion 122, and an insertion opening 123. The support portion 121 has one end thereof connected to the base 110 in order to support the entirety of the irradiation unit 120. The light-emitting portion 122 emits light with which a part of a living body is irradiated. According to the embodiment of the present invention, it is desirable that the color of the light be white. Thus, for example, an incandescent lamp, a halogen lamp, or a white light-emitting diode may be used as a light source of the light-emitting portion 122. The insertion opening 123 is a leading opening through which, for example, a finger 99 is inserted as a part of the living body.

For the light-emitting portion 122, the number of, for example, incandescent lamps or the rated power may be appropriately selected. Solar rays may be used as a light source instead of, for example, incandescent lamps when the entirety of the biological-information obtaining apparatus is exposed to the sun and the finger 99 is placed therebetween.

The image-capturing unit 130 includes a support portion 131 and a camera body 132. The support portion 131 has one end thereof connected to the base 110 and supports the camera body 132. The camera body 132 is used to capture an image of a subject, and may be a general digital still camera or digital video camera or a dedicated camera. It is desirable that the camera body 132 have a continuous shooting mode for shooting a plurality of images in sequence.

A lens unit 133 is provided at a front end of the camera body 132, and is fixed and held by the support portion 131 such that the shooting axis of the lens unit 133 becomes orthogonal to the light-emitting portion 122. The camera body 132 converts the light collected by the lens unit 133 into an electric signal by using an image pickup device. Such an image pickup device may be a one-dimensional line sensor or two-dimensional image sensor that is sensitive to at least two color components, and can be realized by using a charge-coupled device (CCD) sensor or a complementary metal oxide semiconductor (CMOS) sensor. As the image pickup device, one of image pickup devices sensitive to three colors of red (R), green (G), and blue (B) may often be used. In this case, such an image pickup device is usually sensitive to wavelengths from about 800 nm through about 1000 nm. That is, near infrared rays are also receivable.

Images captured by the camera body 132 are sequentially transferred to an image-processing unit 140. The image-processing unit 140 may be achieved using dedicated hardware or using a general personal computer.

Figure 2:
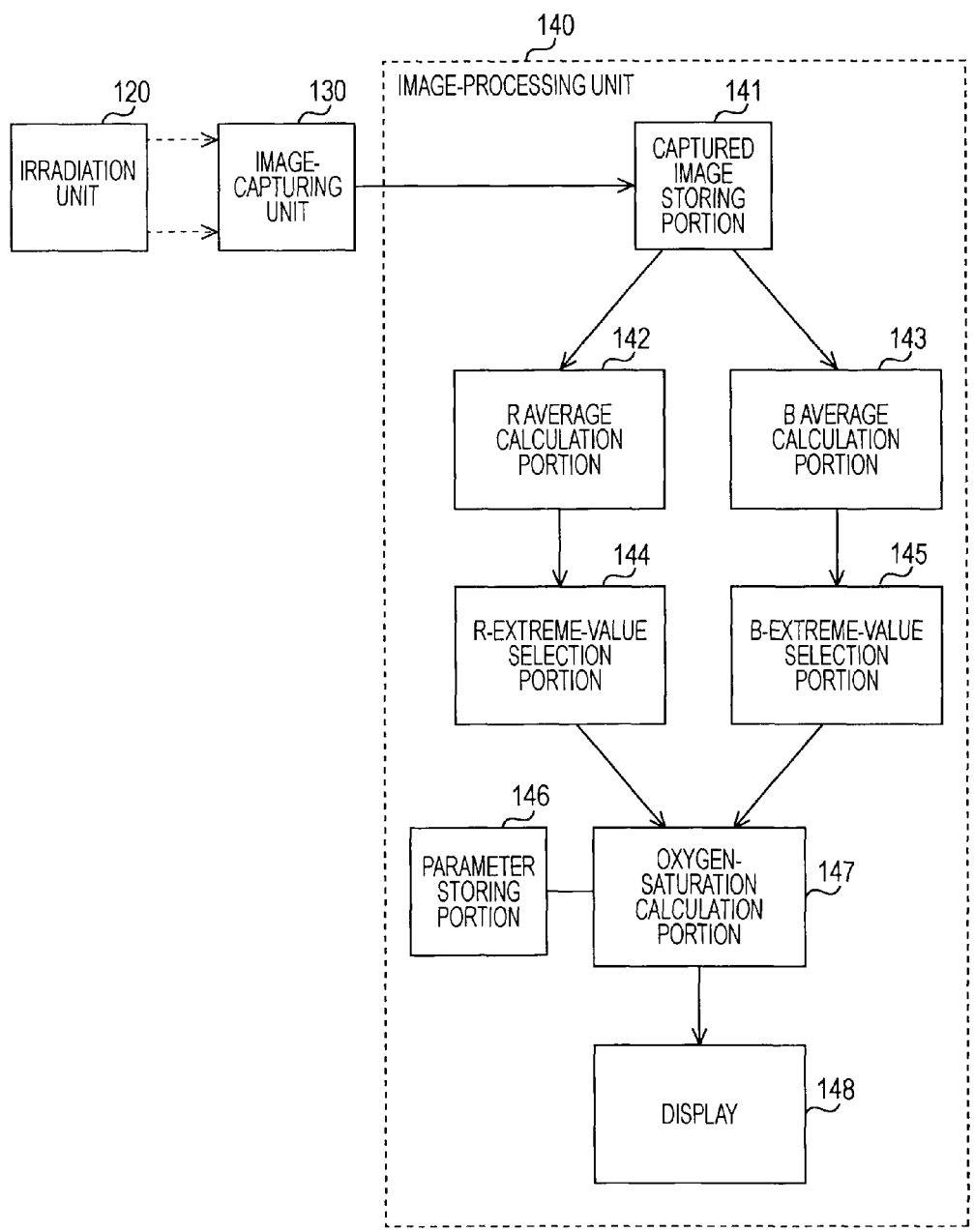
FIG. 2 is a functional block diagram showing an image-processing unit according to the embodiment of the present invention.

FIG. 2 is a functional block diagram showing the image-processing unit 140 according to the embodiment of the present invention. The image-processing unit 140 receives images supplied from the image-capturing unit 130, the images being obtained by irradiating the part of the living body with light emitted by the irradiation unit 120 and by causing the light to be transmitted through the part of the living body. The image-processing unit 140 includes a captured image storing portion 141, an R average calculation portion 142, a B average calculation portion 143, an R-extreme-value selection portion 144, a B-extreme-value selection portion 145, a parameter storing portion 146, a oxygen-saturation calculation portion 147, and a display 148.

The captured image storing portion 141 stores the images supplied from the image-capturing unit 130. The images are captured in time sequence. Here, it is assumed that the number of images is one hundred, corresponding to the number of images captured in five seconds at shooting intervals of twenty images per second. The shooting intervals should be sufficiently shorter than a pulse (wave) cycle. In general, the pulse cycle is approximately 0.5 to 1 second, and thus if the shooting intervals are shorter than 0.1 seconds (that is more than ten images per second), the shooting intervals are sufficiently short. Moreover, it is basically necessary that the overall shooting time period be almost the same as the pulse (wave) cycle; however, in order to perform stable determination, it is desirable that a period of approximately a few seconds be maintained for the overall shooting time period.

The R average calculation portion 142 calculates averages of pixels of the red component for hundred images stored in the captured image storing portion 141. Each of the averages is calculated with respect to a corresponding one of the images stored in the captured image storing portion 141. If time is represented by t (t is an integer, and 1≤t≤100), the averages of the pixels of the red component are expressed by R(t) in time sequence. Here, an average in this case may be the average of the entirety of the captured image; however, if an image of the finger 99 does not appear in the peripheral area of the captured image, an average of a central region (100×100 pixels around a midpoint) of the captured image may be calculated. In addition, a representative point such as the midpoint in the captured image may be used instead of the calculation of the average in order to omit the average calculation process.

The B average calculation portion 143 calculates averages of pixels of the blue component for the hundred images stored in the captured image storing portion 141. Each of the averages is calculated with respect to a corresponding one of the images stored in the captured image storing portion 141. Similarly to the case of the red component, if time is represented by t, the averages of the pixels of the blue component are expressed by B(t) in time sequence. Here, the averages are calculated similarly to the case of the red component.

The R-extreme-value selection portion 144 selects a maximum average and a minimum average in time sequence among the averages R(t) of the pixels of the red component. Here, among the averages R(t), the maximum average is represented by Rc, and the minimum average is represented by Re. Such a maximum or minimum value is called an "extreme".

The B-extreme-value selection portion 145 selects a maximum average and a minimum average in time sequence among the averages B(t) of the pixels of the blue component. Here, among the averages R(t), the maximum average is represented by Bc, and the minimum average is represented by Be.

The parameter storing portion 146 stores known parameters necessary for the calculation of oxygen saturation. Such parameters will be described in detail below.

The oxygen-saturation calculation portion 147 calculates oxygen saturation on the basis of the extremes Rc and Re selected by the R-extreme-value selection portion 144, the extremes Bc and Be selected by the B-extreme-value selection portion 145, and parameters stored in the parameter storing portion 146. A method of calculating the oxygen saturation performed by the oxygen-saturation calculation portion 147 will be described later.

The display 148 displays the oxygen saturation calculated by the oxygen-saturation calculation portion 147. The display 148 may be achieved using, for example, a liquid crystal display (LCD) panel.

Figure 3:
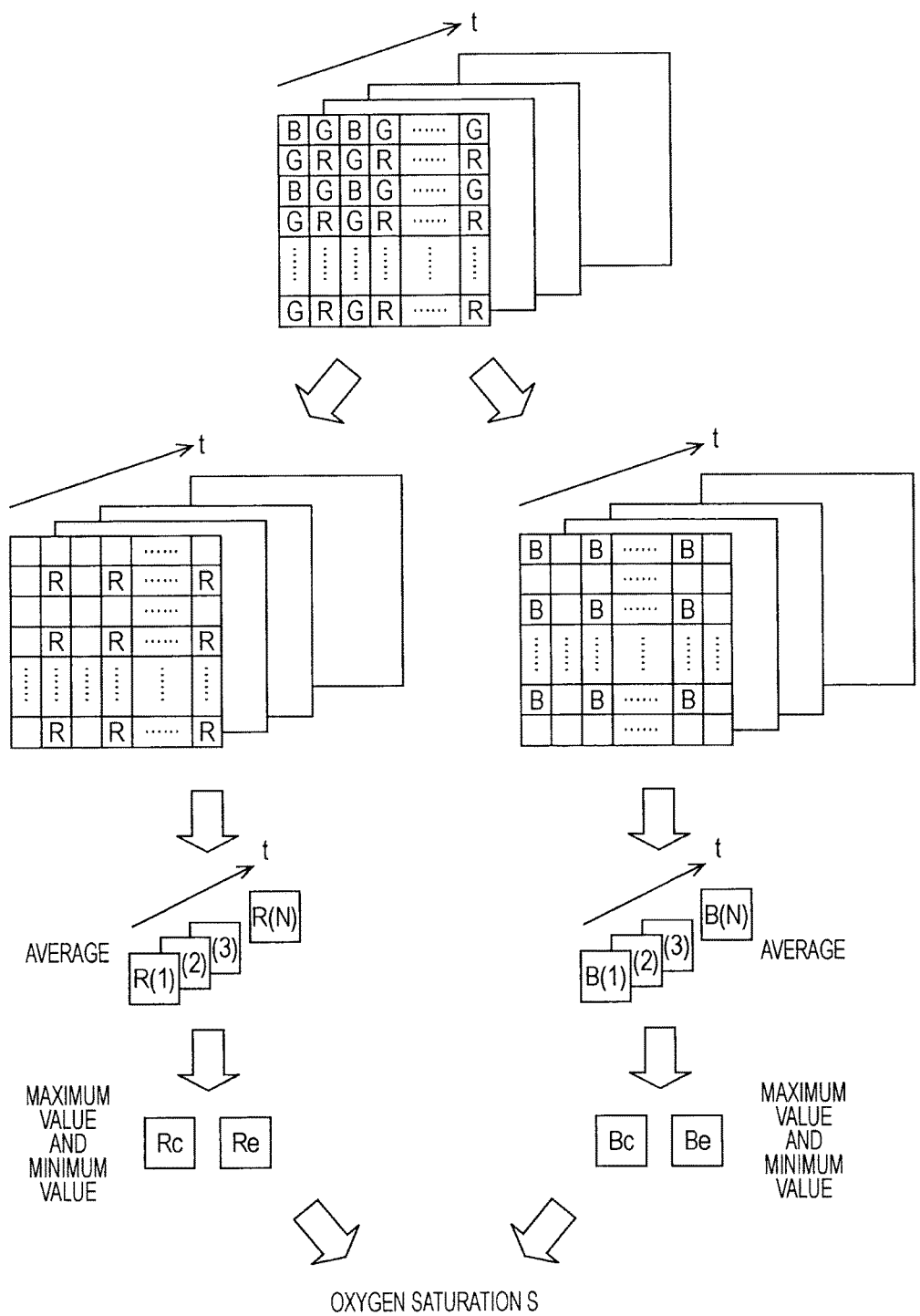
FIG. 3 is a diagram showing a data flow of calculating the oxygen saturation according to the embodiment of the present invention.

FIG. 3 is a diagram showing a data flow of calculating the oxygen saturation according to the embodiment of the present invention. The images captured by the image-capturing unit 130 in time sequence are stored in the captured image storing portion 141. The pixels of the image pickup device are, for example, regularly arranged in a Bayer pattern, and color components can be extracted from the captured images. In this example, the red and blue components are extracted.

With respect to the color components extracted in this way, the R average calculation portion 142 and the B average calculation portion 143 calculate the averages R(t) and B(t) of each of the images captured in time sequence. With respect to the averages R(t) and B(t), the R-extreme-value selection portion 144 and the B-extreme-value selection portion 145 select the extremes (Rc, Re, Bc, and Be) in time sequence.

The extremes selected in this way will be used to calculate the oxygen saturation as shown below. Here, incident light is represented by $I(\lambda)$, transmitted light at the time when arteries are in a shrunk state is represented by $Ic(\lambda)$, transmitted light at the time when arteries are in an expanded state is represented by $Ie(\lambda)$, an absorbance coefficient of oxyhemoglobin is represented by $Eo(\lambda)$, and an absorbance coefficient of deoxyhemoglobin is represented by $Er(\lambda)$. These variables depend on a wavelength $\lambda$. If the incident light $I(\lambda)$ is an incandescent lamp, the proportion of the incident light $I(\lambda)$ at each of wavelengths $\lambda$ can be derived from an expression based on Planck's radiation law regarding blackbody radiation, and is known. Moreover, if the incident light $I(\lambda)$ is sunlight, known experimental data can be utilized for the proportion of the incident light $I(\lambda)$ at each of wavelengths $\lambda$. Here, known experimental data can be utilized for the absorbance coefficient of oxyhemoglobin $Eo(\lambda)$ and the absorbance coefficient of deoxyhemoglobin $Er(\lambda)$.

In addition, if hemoglobin concentration is represented by H, an artery thickness at the time when arteries are in a shrunk state is represented by D, an artery thickness at the time when arteries are in an expanded state is represented by (D+$\delta$), and the oxygen saturation is represented by S, Eq. (1) and Eq. (2) given below are satisfied (Beer-Lambert model).

$$\mathrm{Log}(I(\lambda)/Ic(\lambda)) = \{S \times Eo(\lambda) + (1-S) \times Er(\lambda)\} \times H \times D \quad (1)$$

$$\mathrm{Log}(I(\lambda)/Ie(\lambda)) = \{S \times Eo(\lambda) + (1-S) \times Er(\lambda)\} \times H \times (D+\delta) \quad (2)$$

If spectral sensitivity of the pixels R (spectral characteristics of the R component) is represented by $Tr(\lambda)$, and spectral sensitivity of the pixels B (spectral characteristics of the B component) is represented by $Tb(\lambda)$, the above-described extremes (Rc, Re, Bc, and Be) are expressed by Eq. (3) through Eq. (6) given below. Here, "$\int\sim d\lambda$" means integration with respect to wavelength, and the range of integration includes wavelengths of light received by a certain camera. For example, the range is from 350 nm to 1000 nm.

$$Rc = \int Tr(\lambda) \times Ic(\lambda) d\lambda \quad (3)$$

$$Re = \int Tr(\lambda) \times Ie(\lambda) d\lambda \quad (4)$$

$$Bc = \int Tb(\lambda) \times Ic(\lambda) d\lambda \quad (5)$$

$$Be = \int Tb(\lambda) \times Ie(\lambda) d\lambda \quad (6)$$

By solving Eq. (1) through Eq. (6), the oxygen saturation S can be obtained. In this case, approximation shown below can be performed. Modifying of Eq. (1) through Eq. (6) leads to Eq. (7) given below. The range of integration in this case also falls within the wavelengths of light receivable by the camera. For example, the range of integration is from 350 nm to 1000 nm.

$$\{(Rc-Bc)-(Re-Be)\}/\{Bc-Be\} = \quad (7)$$
$$\int \{Tr(\lambda) - Tb(\lambda)\} \times Ie(\lambda) \times \{S \times Eo(\lambda) + (1-S) \times Er(\lambda)\} d\lambda \Big/$$
$$\int Tb(\lambda) \times Ie(\lambda) \times \{S \times Eo(\lambda) + (1-S) \times Er(\lambda)\} d\lambda$$

Here, since $\delta$ is significantly small in this expression modification process, approximation can be performed according to Eq. (8) given below.

$$\exp\{S \times Eo(\lambda) + (1-S) \times Er(\lambda)\} \times H \times \delta = \quad (8)$$
$$1 + \{S \times Eo(\lambda) + (1-S) \times Er(\lambda)\} \times H \times \delta$$

The transmitted light $Ie(\lambda)$ represents the wavelength $\lambda$ component of light incident on the camera. Since the value of this component decreases exponentially with respect to the absorbance coefficient of oxyhemoglobin $Eo(\lambda)$ and the absorbance coefficient of deoxyhemoglobin $Er(\lambda)$, and the absorbance coefficient of oxyhemoglobin $Eo(\lambda)$ and the absorbance coefficient of deoxyhemoglobin $Er(\lambda)$ become large in a case in which the wavelength $\lambda$ is 600 nm or less, the two ranges of integration on the right side of Eq. (7) may be limited to the range from 600 nm to 1000 nm. On the basis of the similar reasons, the range of integration on the right side of Eqs. (3) through (6) may also be limited to the range from 600 nm to 1000 nm. Moreover, in the case of 800 nm or more, the spectral characteristics of the R component and the spectral characteristics of the B component become almost the same, and thus $Tr(\lambda)-Tb(\lambda)=0$. Therefore, for a fraction on the right side of Eq. (7), the range of integration from 600 nm to 1000 nm is substantially the same as the range of integration from 600 nm to 800 nm. If the absorbance coefficient of oxyhemoglobin Eo(λ) and the absorbance coefficient of deoxyhemoglobin Er(λ) in the range from 600 nm to 800 nm are approximated by Eo(700 nm) and Er(700 nm), respectively, the fraction on the right side of Eq. (7) can be approximated by Eq. (9) given below. Here, the range of integration in Eq. (9) is from 600 nm to 1000 nm.

$$\int \{Tr(\lambda) - Tb(\lambda)\} \times Ie(\lambda) \times \{S \times Eo(\lambda) + (1-S) \times Er(\lambda)\} d\lambda = \quad (9)$$

$$\left\{ \int \{Tr(\lambda) - Tb(\lambda)\} \times Ie(\lambda) d\lambda \right\} \times$$

$$\{S \times Eo(700 \text{ nm}) + (1-S) \times Er(700 \text{ nm})\} =$$

$$\left\{ \int Tr(\lambda) \times Ie(\lambda) d\lambda - \int Tb(\lambda) \times Ie(\lambda) d\lambda \right\} \times$$

$$\{S \times Eo(700 \text{ nm}) + (1-S) \times Er(700 \text{ nm})\} =$$

$$(Re - Be) \times \{S \times Eo(700 \text{ nm}) + (1-S) \times Er(700 \text{ nm})\}$$

The spectral characteristic of the B component is approximately zero in the range from 600 nm to 800 nm, and thus Tb(λ)=0. Therefore, although the denominator on the right side of Eq. (7) indicates that the range of the integration is from 600 nm to 1000 nm, the range of the integration is substantially from 800 nm to 1000 nm. If the absorbance coefficient of oxyhemoglobin Eo(λ) and absorbance coefficient of deoxyhemoglobin Er(λ) in the range from 800 nm to 1000 nm are approximated by Eo(900 nm) and Er(900 nm), respectively, the denominator on the right side of Eq. (7) can be approximated by Eq. (10) given below. Here, the range of the integration in Eq. (10) is from 600 nm to 1000 nm.

$$\int Tb(\lambda) \times Ie(\lambda) \times \{S \times Eo(\lambda) + (1-S) \times Er(\lambda)\} d\lambda = \quad (10)$$

$$\left\{ \int Tb(\lambda) \times Ie(\lambda) d\lambda \right\} \times \{S \times Eo(900 \text{ nm}) + (1-S) \times Er(900 \text{ nm})\} =$$

$$Be \times \{S \times Eo(900 \text{ nm}) + (1-S) \times Er(900 \text{ nm})\}$$

Therefore, Eq. (11) given below can be obtained.

$$\{(Rc - Bc) - (Re - Be)\} / \{Bc - Be\} = \quad (11)$$

$$\frac{[(Re - Be) \times \{S \times Eo(700 \text{ nm}) + (1-S) \times Er(700 \text{ nm})\}]}{[Be \times \{S \times Eo(900 \text{ nm}) + (1-S) \times Er(900 \text{ nm})\}]}$$

Here, Eo(700 nm)=290, Er(700 nm)=1794.28, Eo(900 nm)=1198, and Er(900 nm)=761.84 are known, where all units are cm$^{-1}$/(mol/l). These values are prestored in the parameter storing portion 146 as parameters. The extremes (Rc, Re, Bc, and Be) are selected by the R-extreme-value selection portion 144 and the B-extreme-value selection portion 145 on the basis of the determined values. Since the only unknown parameter is the oxygen saturation S in Eq. (11), information on the oxygen saturation S can be obtained by solving Eq. (11).

Here, the oxygen saturation S calculated according to Beer-Lambert model utilized in the embodiment of the present invention is known for the existence of an error between the calculated value and the actual value, the error occurring under certain conditions. A pulse oximeter of the related art may perform calibration by utilizing this characteristic. In a similar way, the oxygen saturation S can be corrected on the basis of this characteristic in the embodiment of the present invention.

Next, an operation of the biological-information obtaining apparatus according to the embodiment of the present invention will be described with reference to the attached drawings.

Figure 4:
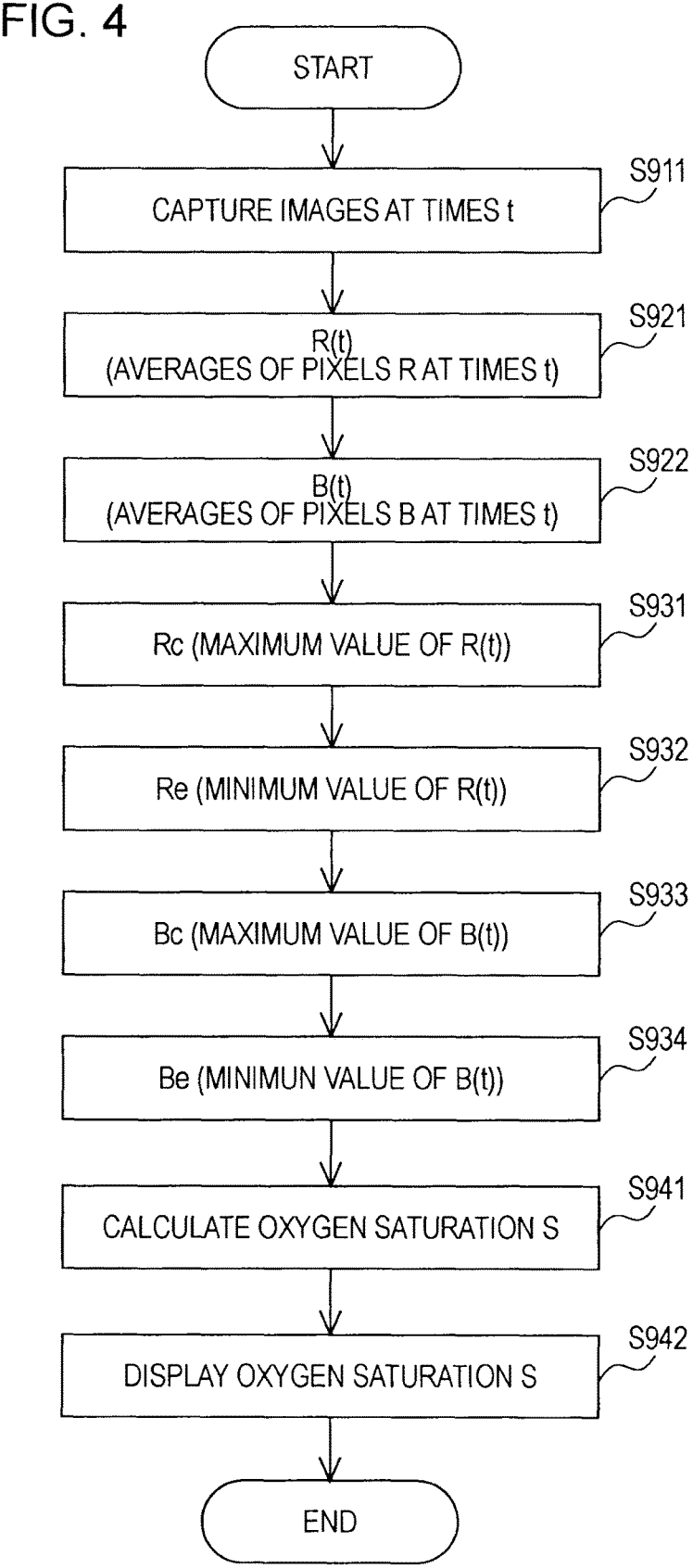
FIG. 4 is a flowchart showing an exemplary process of a biological information obtaining method according to the embodiment of the present invention.

FIG. 4 is a flowchart showing an exemplary process of a biological information (oxygen saturation) obtaining method according to the embodiment of the present invention. In step S911, images captured by the image-capturing unit 130 at times t in time sequence are stored in the captured image storing portion 141.

In step S921, for each of the images captured at times t, the R average calculation portion 142 calculates the average R(t) of the pixels of the red component. In step S922, for each of the images captured at times t, the B average calculation portion 143 calculates the average B(t) of the pixels of the blue component.

The R-extreme-value selection portion 144 selects extremes among averages R(t) calculated in step S921. The B-extreme-value selection portion 145 selects extremes among averages B(t) calculated in step S922. That is, in step S931, the maximum average among the averages R(t) of the pixels of the red component is selected as Rc, and in step S932, the minimum average among the averages R (t) of the pixels of the red component is selected as Re. In step S933, the maximum average among the averages B(t) of the pixels of the blue component is selected as Bc, and in step S934, the minimum average among the averages B(t) of the pixels of the blue component is selected as Be.

The oxygen-saturation calculation portion 147 calculates the oxygen saturation S on the basis of the extremes (Rc, Re, Bc, and Be) selected in steps S931 through S934. Eq. (11) can be used to calculate the oxygen saturation S. In step S942, the calculated oxygen saturation S is displayed on the display 148.

In this way, according to the embodiment of the present invention, with respect to the pixels of two colors included in the images captured in time sequence, the R-extreme-value selection portion 144 and the B-extreme-value selection portion 145 select the extremes in time sequence. The oxygen-saturation calculation portion 147 can calculate the oxygen saturation S according to Eq. (11) on the basis of these extremes.

According to the embodiment of the present invention, the example in which the combination of R and B among three colors of R, G, and B is used. However, instead of this combination, the combination of R and G or the combination of B and G may also be used to calculate the oxygen saturation S.

The biological-information obtaining apparatus according to the embodiment of the present invention can be used as a vein authentication apparatus. That is, the use of such a vein authentication apparatus can achieve both identifying of an individual on the basis of vein authentication and obtaining of biological information (information regarding health) regarding the individual. For example, oxygen saturation of a plurality of patients may be successively determined by using a single pulse oximeter for a short period of time in large hospitals. In this case, which determined oxygen saturation belonging to which patient is manually recorded in a medical certificate. Thus, the determined oxygen saturation may be linked to a wrong patient. However, if the biological-information obtaining apparatus according to the embodiment of the present invention is used, when oxygen saturation is determined, which determined oxygen saturation belonging to which patient can be simultaneously specified by vein authentication. That is, a single apparatus can output "identified patient data" and "oxygen-saturation data for the identified patient" as a pair of pieces of electronic data. The patient's electronic medical record is made using this pair of pieces of the electronic data, and thus human error can be largely reduced.

As the embodiment of the present invention, an example of an achieved apparatus of transmissive type has been described above. Similarly to the case in which there are pulse oximeters of transmissive type and of reflective type, the apparatus according to the embodiment of the present invention is not limited to being an apparatus of transmissive type and may be an apparatus of reflective type. That is, a structure (of reflective type) in which a light-emitting unit and a light-receiving unit are disposed on the same side of a finger may be employed instead of the structure (of transmissive type) in which a light-emitting unit and a light-receiving unit are disposed on opposite sides of the finger.

The embodiment of the present invention is illustrated as an example of a way to realize the present invention. Although there is a correspondence between the embodiment and the features of the claims, which will be described below, the present invention is not limited thereto, and various modifications can be made without departing from the spirit and scope of the present invention.

That is, according to an embodiment of the present invention, light-emitting means corresponds to, for example, the light-emitting portion 122. Image-capturing means corresponds to, for example, the image-capturing unit 130. Extreme generation means corresponds to, for example, the R average calculation portion 142, the B average calculation portion 143, the R-extreme-value selection portion 144, and the B-extreme-value selection portion 145. Oxygen-saturation calculation means corresponds to, for example, the oxygen-saturation calculation portion 147.

According to another embodiment of the present invention, light-emitting means corresponds to, for example, the light-emitting portion 122. Image-capturing means corresponds to, for example, the image-capturing unit 130. An extreme generation process corresponds to, for example, steps S931 through S934. An oxygen-saturation calculation process corresponds to, for example, step S941.

The processes described in the embodiment of the present invention may be considered as a method having the series of processes or may be considered as a program for allowing a computer to execute the series of processes or as a recording medium having the program recorded thereon.

It should be understood by those skilled in the art that various modifications, combinations, sub-combinations and alterations may occur depending on design requirements and other factors insofar as they are within the scope of the appended claims or the equivalents thereof.

What is claimed is:

1. A biological-information obtaining apparatus comprising:

light-emitting means for emitting light;

image-capturing means for capturing images, in time sequence, obtained by irradiating a living body with the light emitted and by causing the light to be transmitted through or reflected by the living body, the image-capturing means being sensitive to at least two color components;

extreme generation means for generating a maximum value and a minimum value, in time sequence, of each of the color components for certain regions of the captured images; and oxygen-saturation calculation means for calculating oxygen saturation on the basis of the maximum value and the minimum value of each of the color components.

2. The biological-information obtaining apparatus according to claim 1, wherein the light-emitting means emits white light.

3. The biological-information obtaining apparatus according to claim 1, wherein the color components include red and blue.

4. The biological-information obtaining apparatus according to claim 1, wherein the extreme generation means generates, for each of the color components, the maximum value and the minimum value in the time sequence from averages of the color component for the entirety of the captured images.

5. The biological-information obtaining apparatus according to claim 1, wherein the extreme generation means generates, for each of the color components, the maximum value and the minimum value in the time sequence from averages of the color component for predetermined regions of the captured images.

6. A biological-information obtaining apparatus comprising:

light-emitting means for emitting white light;

image-capturing means for capturing images, in time sequence, obtained by irradiating a living body with the light emitted and by causing the light to be transmitted through or reflected by the living body, the image-capturing means being sensitive to at least red and blue color components;

extreme generation means for generating a maximum value and a minimum value, in time sequence, of each of the color components for certain regions of the captured images; and oxygen-saturation calculation means for calculating, on the basis of the maximum value and the minimum value of each of the color components, oxygen saturation by solving an equation of $\{(Rc-Bc)-(Re-Be)\}/\{Bc-Be\}=[(Re-Be)\times\{S\times Eo(\lambda 1)+(1-S)\times Er(\lambda 1)\}]/[Be\times\{S\times Eo(\lambda 2)+(1-S)\times Er(\lambda 2)\}]$, where Rc represents the maximum value of the red component, Bc represents the maximum value of the blue component, Re represents the minimum value of the red component, Be represents the minimum value of the blue component, S represents oxygen saturation, $Eo(\lambda)$ represents a known absorbance coefficient of oxyhemoglobin at a wavelength $\lambda$, $Er(\lambda)$ represents a known absorbance coefficient of deoxyhemoglobin at a wavelength $\lambda$, and $\lambda 1$ and $\lambda 2$ represent specific values of wavelength $\lambda$.

7. A method of obtaining biological information, the method being performed by a biological-information obtaining apparatus including light-emitting means for emitting white light, and image-capturing means for capturing images, in time sequence, obtained by irradiating a living body with the light emitted and by causing the light to be transmitted through or reflected by the living body, the image-capturing means being sensitive to at least red and blue color components, the method comprising the steps of:

generating a maximum value and a minimum value, in time sequence, of each of the color components for certain regions of the captured images; and calculating oxygen saturation by solving an equation of $\{(Rc-Bc)-(Re-Be)\}/\{Bc-Be\}=[(Re-Be)\times\{S\times Eo(\lambda 1)+(1-S)\times Er(\lambda 1)\}]/[Be\times\{S\times Eo(\lambda 2)+(1-S)\times Er(\lambda 2)\}]$, where Rc represents the maximum value of the red component, Bc represents the maximum value of the blue component, Re represents the minimum value of the red component, Be represents the minimum value of the blue component, S represents oxygen saturation, $Eo(\lambda)$ represents a known absorbance coefficient of oxyhemoglobin at a wavelength $\lambda$, $Er(\lambda)$ represents a known absorbance coefficient of deoxyhemoglobin at a wavelength $\lambda$, and $\lambda 1$ and $\lambda 2$ represent specific values of wavelength $\lambda$.

8. A biological-information obtaining apparatus comprising:

a light-emitting unit configured to emit light;

an image-capturing unit configured to capture images, in time sequence, obtained by irradiating a living body with the light emitted and by causing the light to be transmitted through or reflected by the living body, the image-capturing unit being sensitive to at least two color components;

an extreme generation unit configure to generate a maximum value and a minimum value, in time sequence, of each of the color components for certain regions of the captured images; and an oxygen-saturation calculation unit configured to calculate oxygen saturation on the basis of the maximum value and the minimum value of each of the color components.

9. A biological-information obtaining apparatus comprising:

a light-emitting unit configured to emit white light;

an image-capturing unit configured to capture images, in time sequence, obtained by irradiating a living body with the light emitted and by causing the light to be transmitted through or reflected by the living body, the image-capturing unit being sensitive to at least red and blue color components;

an extreme generation unit configured to generate a maximum value and a minimum value, in time sequence, of each of the color components for certain regions of the captured images; and an oxygen-saturation calculation unit configured to calculate, on the basis of the maximum and the minimum of each of the color components, oxygen saturation by solving an equation of $\{(Rc-Bc)-(Re-Be)\}/\{Bc-Be\}=[(Re-Be)\times\{S\times Eo(\lambda 1)+(1-S)\times Er(\lambda 1)\}]/[Be\times\{S\times Eo(\lambda 2)+(1-S)\times Er(\lambda 2)\}]$, where Rc represents the maximum value of the red component, Bc represents the maximum value of the blue component, Re represents the minimum value of the red component, Be represents the minimum value of the blue component, S represents oxygen saturation, $Eo(\lambda)$ represents a known absorbance coefficient of oxyhemoglobin at a wavelength $\lambda$, $Er(\lambda)$ represents a known absorbance coefficient of deoxyhemoglobin at a wavelength $\lambda$, and $\lambda 1$ and $\lambda 2$ represent specific values of wavelength $\lambda$.

\* \* \* \* \*